United States Patent
Kang

(10) Patent No.: US 9,334,222 B2
(45) Date of Patent: May 10, 2016

(54) DEVICE AND METHOD FOR SEPARATING OFF WATER AND RECOVERING A CARBOXYLIC ACID FROM REACTOR DISCHARGE DURING AN AROMATIC COMPOUND OXIDATION REACTION USING ENERGY DONATING COUPLED DISTILLATION

(75) Inventor: Ki Joon Kang, Gyeonggi-do (KR)

(73) Assignees: AMTPACIFIC CO., LTD, Seoul (KR); Ki Joon Kang, Gyeonggi-Do (KR)

( * ) Notice: Subject to any disclaimer, the term of this patent is extended or adjusted under 35 U.S.C. 154(b) by 76 days.

(21) Appl. No.: 14/344,322

(22) PCT Filed: May 17, 2012

(86) PCT No.: PCT/KR2012/003883
§ 371 (c)(1),
(2), (4) Date: Mar. 12, 2014

(87) PCT Pub. No.: WO2013/039288
PCT Pub. Date: Mar. 21, 2013

(65) Prior Publication Data
US 2014/0343320 A1 Nov. 20, 2014

(30) Foreign Application Priority Data

Sep. 15, 2011 (KR) .................. 10-2011-0092727
Sep. 22, 2011 (KR) .................. 10-2011-0095698

(51) Int. Cl.

| | |
|---|---|
| C07C 51/46 | (2006.01) |
| C07C 53/08 | (2006.01) |
| C07B 63/00 | (2006.01) |
| B01D 3/36 | (2006.01) |
| B01D 5/00 | (2006.01) |
| C07C 51/377 | (2006.01) |
| B01D 3/00 | (2006.01) |

(52) U.S. Cl.
CPC ............ *C07C 51/377* (2013.01); *B01D 3/007* (2013.01); *B01D 3/36* (2013.01); *C07B 63/00* (2013.01); *C07C 51/46* (2013.01); *Y02P 70/34* (2015.11)

(58) Field of Classification Search
CPC ........ C07C 51/46; C07C 53/08; C07B 63/00; B01D 3/36; B01D 5/00
USPC .......... 562/405, 407, 408, 409, 410, 412, 414
See application file for complete search history.

(56) References Cited

U.S. PATENT DOCUMENTS

| | | | |
|---|---|---|---|
| 4,334,086 A * | 6/1982 | Hanotier et al. | 562/413 |
| 2003/0150706 A1* | 8/2003 | Jang et al. | 203/14 |

(Continued)

FOREIGN PATENT DOCUMENTS

| | | |
|---|---|---|
| KR | 10-2006-0124098 A | 12/2006 |
| KR | 10-2008-0000415 A | 1/2008 |

(Continued)

*Primary Examiner* — Kamal Saeed
*Assistant Examiner* — Janet L Coppins
(74) *Attorney, Agent, or Firm* — Revolution IP, PLLC

(57) ABSTRACT

Provided is a method of separating off reaction product water and recovering a carboxylic acid used as a solvent in a reactor from a reactor discharge during oxidation of an aromatic compound, and more particularly, a method of separating off reaction product water and recovering a carboxylic acid used as a solvent in a reactor from a reactor discharge during oxidation of an aromatic compound, wherein during the oxidation of the aromatic compound, the reactor discharge is led into two or more dehydration towers having different operating pressures such that a condenser of one dehydration tower operates as a reboiler of another dehydration tower, thereby remarkably reducing energy consumption.

3 Claims, 5 Drawing Sheets

(56) References Cited

U.S. PATENT DOCUMENTS

2005/0272951 A1* 12/2005 Noe' .............................. 562/412
2009/0293722 A1   12/2009 Svendsen et al.

FOREIGN PATENT DOCUMENTS

| KR | 10-0794317 B1 | 1/2008 |
| KR | 10-2009-0039274 A | 4/2009 |

* cited by examiner

DEVICE AND METHOD FOR SEPARATING OFF WATER AND RECOVERING A CARBOXYLIC ACID FROM REACTOR DISCHARGE DURING AN AROMATIC COMPOUND OXIDATION REACTION USING ENERGY DONATING COUPLED DISTILLATION

CROSS REFERENCE TO PRIOR APPLICATIONS

This application is a National Stage Application of PCT International Patent Application No. PCT/KR2012/003883 filed on May 17, 2012, under 35 U.S.C. §371, which claims priority to Korean Patent Application Nos. 10-2011-0092727 filed on Sep. 15, 2011 and 10-2011-0095698 filed on Sep. 22, 2011, which are all hereby incorporated by reference in their entirety.

TECHNICAL FIELD

The present invention relates to a method of separating off water and recovering a carboxylic acid from a reactor discharge during aromatic compound oxidation using energy donating coupled distillation, and more particularly, to a method of economically separating off water and recovering a carboxylic acid from a reactor discharge during oxidation of an aromatic compound while remarkably reducing consumption of steam used to separate off the water and the carboxylic acid during a general well-known distillation or azeotropic distillation process by using two dehydration towers having different operating pressures to separate off the water and recover the carboxylic acid from the reactor discharge during the oxidation of the aromatic compound, wherein a condenser of the dehydration tower having a high operating pressure operates as a reboiler of the dehydration tower having a low operating pressure such that energy is shared.

BACKGROUND ART

Generally, when an aromatic compound is oxidized, the aromatic compound generates heat and an aromatic carboxylic acid and water are generated. Since the aromatic carboxylic acid is generally in a solid state, a solvent is injected such that the aromatic carboxylic acid does not exist in the solid state in a reactor. Since solubility of the aromatic carboxylic acid is high in a carboxylic acid, the carboxylic acid is injected into an oxidation reactor such that an aromatic oxide that is a reaction product maintains a liquid state. Accordingly, gas and liquid discharges generated after the oxidation contain much water and carboxylic acid, and thus it is necessary to perform a dehydration process so as to remove the water generated via the oxidation and recover the carboxylic acid back to the oxidation reactor.

In detail, processes for manufacturing a compound of a phthalic acid that is a type of aromatic carboxylic acid include an oxidation process for oxidizing an aromatic compound by air using a catalyst, such as a cobalt, manganese, or bromine, and a dehydration process for removing water and recovering an acetic acid that is a type of carboxylic acid used as a solvent in a reactor.

Here, a dehydration tower for recovering the acetic acid at a lower part and separating off the water at a top part is driven such that concentration of the acetic acid recovered at the lower part is generally from 90 to 95 wt %. Since a boiling temperature of a solution containing 90 to 90 wt % acetic acid at the lower part of the dehydration tower is from about 108 to about 111° C. under an atmospheric pressure, and a boiling temperature of the water at the top part of the dehydration tower is 100° C. under an atmospheric pressure, two or more dehydration towers may be used by setting a pressure difference between the dehydration towers to be about 1 kg/cm² or lower. At this time, a condenser of the dehydration tower having a high pressure may operate as a reboiler of the dehydration tower having a low pressure, and thus the two or more dehydration towers may be driven via energy supplied to the reboiler of one dehydration tower even with a low pressure difference, thereby reducing energy based on a principle of multi-effect evaporator. The present invention is invented based on such features.

An acetic acid that is a type of carboxylic acid may be separated from water via conventional distillation or azeotropic distillation wherein an acetate compound or alcohol is circulated, and at this time, since a temperature of a lower part of a distillation tower is high, i.e., from about 125 to about 135° C., due to a pressure loss in a dehydration tower, a type of steam used in a reboiler is medium pressure steam (3.0 to 5 kg/cm²G and 143 to 158° C.).

Also, a lot of medium pressure steam is used to maintain concentration of an acetic acid in a discharge to be 0.5 wt % during conventional distillation and maintain concentration of an acetic acid in discharge to be 0.01 wt % during azeotropic distillation, so as to increase a recovery rate of the acetic acid and reduce waste water disposal costs.

FIG. 1 is a diagram for describing a method of recovering an acetic acid through conventional distillation.

Referring to FIG. 1, an apparatus for recovering an acetic acid through conventional distillation includes a dehydration tower 1, a reboiler, a condenser 3, and a condensate drum 4. A liquid stream having a low acetic acid concentration (acetic acid concentration: 40 to 70 wt %) and a gas stream having a high acetic acid concentration (acetic acid concentration: 70 to 88 wt %) are led into the dehydration tower 1, a portion of the acetic acid (acetic acid concentration: 88 to 95 wt %) from a lower part of the dehydration tower 1 is externally discharged while a remaining portion is led into the dehydration tower 1 again through the reboiler 2, and a non-condensate gas in a condensate that is from a top part of the dehydration tower 1 and passed through the condensate drum 4 selectively provided through the condenser 3 is externally discharged as a vent gas while some of the condensate is led into the dehydration tower 1 again as a reflux solution.

Consumption of medium pressure steam by a dehydration tower to dewater and recover an acetic acid through the conventional distillation is about 90 to 100 tons per hour in a factory generating 500,000 tons of phthalic acid per year.

FIG. 2 is a diagram for describing a method of recovering an acetic acid through azeotropic distillation.

Briefly describing with reference to FIG. 2, an apparatus for recovering an acetic acid through azeotropic distillation by using a conventional azeotropic agent includes an acetic acid recovering device 5 including the dehydration tower 1 for separating off an acetic acid and water through azeotropic distillation, the condenser 3 for condensing a gas discharged from the top part of the dehydration tower 1, an oil separator 4a for separating off an organic material (organic phase) and water (aqueous phase) of a liquid that passed through the condenser 3, the reboiler 2 for supplying steam to the dehydration tower 1, and an external azeotropic agent storage unit (not shown). The apparatus selectively includes an organic material recovering device 6 for recovering an organic material from a water phase stream of the acetic acid recovering device 5, an azeotropic agent recovering device 7 for recovering an azeotropic agent from an oil phase stream of the acetic acid recovering device 5, and an aromatic compound recovering device 8 for recovering an aromatic compound from the acetic acid recovering device 5. Detailed processes of the method of FIG. 2 are shown in FIG. 2.

Consumption of medium pressure steam by a dehydration tower to recover an acetic acid through azeotropic distillation is about 60 to 70 tons per hour in a factory generating 500,000 tons of phthalic acid per year, and total consumption of medium pressure steam is about 65 to 75 tons per hour when consumption of medium pressure steam by distillation towers operated to recover an azeotropic agent is added. Consumption of medium pressure steam during a method of recovering an acetic acid by using an azeotropic agent is less than that used during a method of recovering an acetic acid by using conventional distillation by about 25 to 30%, but a portion of the azeotropic agent may generate impurities by being lost in an oxidation reactor while a portion of the azeotropic agent cannot be completely prevented from being discharged with waste water.

DETAILED DESCRIPTION OF THE INVENTION

Technical Problem

The present invention provides a method and apparatus for separating off water generated from a discharge discharged from a reactor via oxidation and recovering a carboxylic acid used as a solvent, during the oxidation of an aromatic compound using energy donating coupled distillation, wherein consumption of energy by a dehydration tower is lesser than that during a conventional distillation process, and since an azeotropic agent is not used, a storage unit for storing an azeotropic agent is not required, a separate distillation tower for recovering an azeotropic agent may not be operated, and an azeotropic agent may not be lost.

The present invention also provides a method and apparatus for separating off water generated from a discharge discharged from a reactor via oxidation and recovering a carboxylic acid used as a solvent, during the oxidation of an aromatic compound using energy donating coupled distillation, wherein consumption of energy may be reduced even when azeotropic distillation using an azeotropic agent is employed by configuring two dehydration towers sharing energy.

Technical Solution

According to an aspect of the present invention, there is provided an apparatus for separating off water and recovering a carboxylic acid from a discharge discharged from a reactor during oxidation of an aromatic compound using energy donating coupled distillation, the apparatus including: first and second dehydration towers sharing energy; a first dehydration tower condenser provided at a downstream of a top part of the first dehydration tower; a first dehydration tower condensate drum, a first dehydration tower condensate transfer pump, and a first dehydration tower condensate vacuum pump, which are selectively provided at a downstream of the first dehydration tower condenser; a first dehydration tower reboiler-second dehydration tower condenser (energy sharing heat exchanger) for re-boiling and condensing a discharge by being commonly connected to a downstream of a lower part of the first dehydration tower and a downstream of a top part of the second dehydration tower; a second dehydration tower cooler and a second dehydration tower condensate drum, which are sequentially provided at a downstream of the first dehydration tower reboiler-second dehydration tower condenser (energy sharing heat exchanger), wherein the second dehydration tower condensate drum is selectively provided; and a second dehydration tower reboiler provided at a downstream of a lower part of the second dehydration tower.

According to another aspect of the present invention, there is provided an apparatus (when including azeotropic distillation) for separating off water and recovering a carboxylic acid from a discharge discharged from a reactor during oxidation of an aromatic compound using energy donating coupled distillation, the apparatus including: a first carboxylic acid recovering device including a first dehydration tower for separating any stream containing a carboxylic acid or a liquid stream having a relatively low carboxylic acid concentration into a carboxylic acid and water via conventional distillation, a first condenser for condensing a gas discharged to a top part of the first dehydration tower, a first condensate drum selectively provided to store a condensate that passed through the first condenser, and a first reboiler for supplying energy to the first dehydration tower, wherein the first reboiler shares energy with a second condenser at a top part of a second dehydration tower that is an azeotropic distillation tower; and a second carboxylic acid recovering device provided at the rear of the first carboxylic acid recovering device and including the second dehydration tower for azeotropic distillation into which a stream formed of another carboxylic acid and water is selectively led and into which a discharge from the first dehydration tower is led, the second condenser for condensing a gas discharged to a top part of the second dehydration tower through the first reboiler, an oil separator provided at a rear of the second condenser, and a second reboiler for supplying energy to the second dehydration tower, wherein the apparatus selectively includes an organic material recovering device for recovering an organic material from a water phase stream from the second carboxylic acid recovering device, an azeotropic agent recovering device for recovering an azeotropic agent from an oil phase stream of the second carboxylic acid recovering device, and an aromatic compound recovering device for recovering an aromatic compound from the second carboxylic acid recovering device. A vent gas may be discharged as a vacuum pump is selectively provided at one side of a downstream of the first condensate drum if the first carboxylic acid recovering device, and an discharge condensate may be led into the second dehydration tower as a transfer pump is selectively provided at another side of the downstream. Here, the organic material recovering device, the azeotropic agent recovering device, and the aromatic compound recovering device may each include a distillation tower, a reboiler, a condenser, and a condensate drum, which are basic components for recovering an acetic acid via conventional distillation.

According to another aspect of the present invention, there is provided an apparatus for separating off water and recovering a carboxylic acid from a discharge discharged from a reactor during oxidation of an aromatic compound using energy donating coupled distillation, the apparatus including: a first carboxylic acid recovering device including a first dehydration tower for separating a carboxylic acid and water via conventional distillation, a first condenser for condensing a gas discharged to a top part of the first dehydration tower, a first condensate drum selectively provided to store a condensate that passed through the first condenser, and a first reboiler for supplying energy to the first dehydration tower, wherein the first reboiler shares energy with a second condenser at a top part of a second dehydration tower that is an azeotropic distillation tower; and a second carboxylic acid recovering device provided at the rear of the first carboxylic acid recovering device and including the second dehydration tower for azeotropic distillation into which a stream formed of another carboxylic acid and water is selectively led and into which a discharge from an extraction tower is led, the second condenser for condensing a gas discharged to a top part of the second dehydration tower through the first reboiler, an oil separator provided at a rear of the second condenser, and a second reboiler for supplying energy to the second dehydration tower, wherein the apparatus selectively includes an organic material recovering device for recovering an organic material from a water phase stream from the second carboxylic acid recovering device, an azeotropic agent recovering device for recovering an azeotropic agent from an oil phase stream of the second carboxylic acid recovering device, an aromatic compound recovering device for recovering an aromatic compound from the second carboxylic acid recovering device, and an extracting device in which water containing a low concentration carboxylic acid discharged from a top part of the first dehydration tower of the first carboxylic acid recovering device is led into a top part and an azeotropic agent discharged to a top part of the second dehydration tower of the second carboxylic acid recovering device is led into a lower part as an extracting agent such that the top part transfers a mixture of the extracting agent, the carboxylic acid, and the water to the second dehydration tower and the lower part selectively transfers the water to the organic material recovering device. A vent gas may be discharged as a vacuum pump is selectively provided at one side of a downstream of the first condensate drum if the first carboxylic acid recovering device, and an discharge condensate may be led into the second dehydration tower as a transfer pump is selectively provided at another side of the downstream. Here, the organic material recovering device, the azeotropic agent recovering device, and the aromatic compound recovering device may each include a distillation tower, a reboiler, a condenser, and a condensate drum, which are basic components for recovering an acetic acid via conventional distillation. Also, the extracting device includes a general extraction tower using an extracting agent or an extraction tower including a driving device.

According to another aspect of the present invention, there is provided a method of separating off water and recovering a carboxylic acid from a discharge discharged from a reactor during oxidation of an aromatic compound using energy donating coupled distillation, the method including: flowing the discharge into a first dehydration tower that is in a decompressed or atmospheric state after the discharge passes through each device for processes so as to discharge water to a top part of the first dehydration tower and recover a first concentrated carboxylic acid to a lower part of the first dehydration tower; and flowing the first concentrated carboxylic acid discharged from the lower part of the first dehydration tower into a center of a second dehydration tower that is in an atmospheric or pressurized state so as to recover a final concentrated carboxylic acid to a lower part of the second dehydration tower, wherein a condenser of the second dehydration tower operates as a reboiler of the first dehydration tower such that energy supplied to a reboiler of the second dehydration tower is used as distillation energy of the first dehydration tower.

According to another aspect of the present invention, there is provided a method of separating off water and recovering a carboxylic acid from a discharge discharged from a reactor during oxidation of an aromatic compound using energy donating coupled distillation, the method including: flowing the discharge into a first dehydration tower that is in a decompressed or atmospheric state after the discharge passes through each device for processes so as to recover a concentrated carboxylic acid at a lower part of the first dehydration tower and discharge water from which a carboxylic acid is not fully removed to a top part of the first dehydration tower; and flowing the water discharged to the top part of the first dehydration tower into a center of a second dehydration tower in an atmospheric or pressurized state, wherein the second dehydration tower is configured as an azeotropic distillation tower, so as to recover a carboxylic acid at a lower part of the second dehydration tower and discharge finally separated water to a top part of the second dehydration tower by using an azeotropic agent, wherein a condenser of the second dehydration tower operates as a reboiler of the first dehydration tower such that energy supplied to a reboiler of the second dehydration tower is used as distillation energy of the first dehydration tower.

According to another aspect of the present invention, there is provided a method of separating off water and recovering a carboxylic acid from a discharge discharged from a reactor during oxidation of an aromatic compound using energy donating coupled distillation, the method including: flowing the discharge into a first dehydration tower that is in a decompressed or atmospheric state after the discharge passes through each device for processes so as to recover a concentrated carboxylic acid at a lower part of the first dehydration tower and discharge water from which a carboxylic acid is not fully removed to a top part of the first dehydration tower; flowing water containing a carboxylic acid discharged to the top part of the first dehydration tower into a top part of an extraction tower and flowing an azeotropic agent discharged from an oil separator provided at a downstream of a top part of a second dehydration tower into a lower part of the extraction tower as an extracting agent so as to discharge water from which a carboxylic acid is removed to the lower part of the extraction tower and extract a mixture of the extracting agent, the carboxylic acid, and the water to the top part of the extraction tower; and flowing the mixture discharged to the top part of the extraction tower into a center of the second dehydration tower in an atmospheric or pressurized state, wherein the second dehydration tower is configured as an azeotropic distillation tower, so as to recover a carboxylic acid at a lower part of the second dehydration tower and discharge finally separated water to a top part of the second dehydration tower by using an azeotropic agent, wherein a condenser of the second dehydration tower operates as a reboiler of the first dehydration tower such that energy supplied to a reboiler of the second dehydration tower is used as distillation energy of the first dehydration tower.

Advantageous Effects

As described above, a method of separating off water and recovering a carboxylic acid from a reactor discharge during oxidation of an aromatic compound using energy donating coupled distillation has following effects.

First, consumption of energy required to dewater and recover a carboxylic acid may be reduced since at least two dehydration towers sharing energy are connected to each other to be operated.

Second, consumption of medium pressure steam may be further reduced since low pressure steam that was not required may be used by adding a reboiler using low pressure steam to a lower part of a dehydration tower, when at least one dehydration tower is decompressed to be vacuum-operated.

Third, energy consumption is lower than azeotropic distillation using one dehydration tower, without having to use an azeotropic agent, and thus a separate azeotropic agent storage unit is not required and an azeotropic agent may not be lost.

Fourth, energy consumption may be further reduced even when azeotropic distillation is used, by operating at least two dehydration towers sharing energy.

MODE OF THE INVENTION

Hereinafter, the present invention will be described more fully with reference to the accompanying drawings, in which exemplary embodiments of the invention are shown.

Methods and apparatuses for separating off water generated via a reaction and recovering an acetic acid that is a representative type of a carboxylic acid used as a solvent in a reactor during a process of manufacturing a phthalic acid that is a type of an aromatic carboxylic acid generated by oxidizing p-xylene that is a type of an aromatic compound in air using energy donating coupled distillation, according to one or more embodiments of the present invention will now be described.

For reference, the inventor designed the present invention based on the fact that consumption of medium pressure steam may be reduced by using a multi-effect evaporator, because when at least two dehydration towers having different operating pressures are used, energy required in a reboiler of a preceding dehydration tower may be provided to a condenser of a following dehydration tower while separating off water and recovering an acetic acid from discharges during oxidation of manufacturing a phthalic acid, wherein an acetic acid used as a solvent and water generated via a reaction are discharged in gas states at a high temperature together with a gas, such as nitrogen in air, due to heat generated when p-xylene is oxidized by air by using cobalt (Co), manganese (Mn), and bromine (Br) catalysts in a reactor, and some acetic acid and water are discharged in liquid states together with the phthalic acid.

Figure 1:
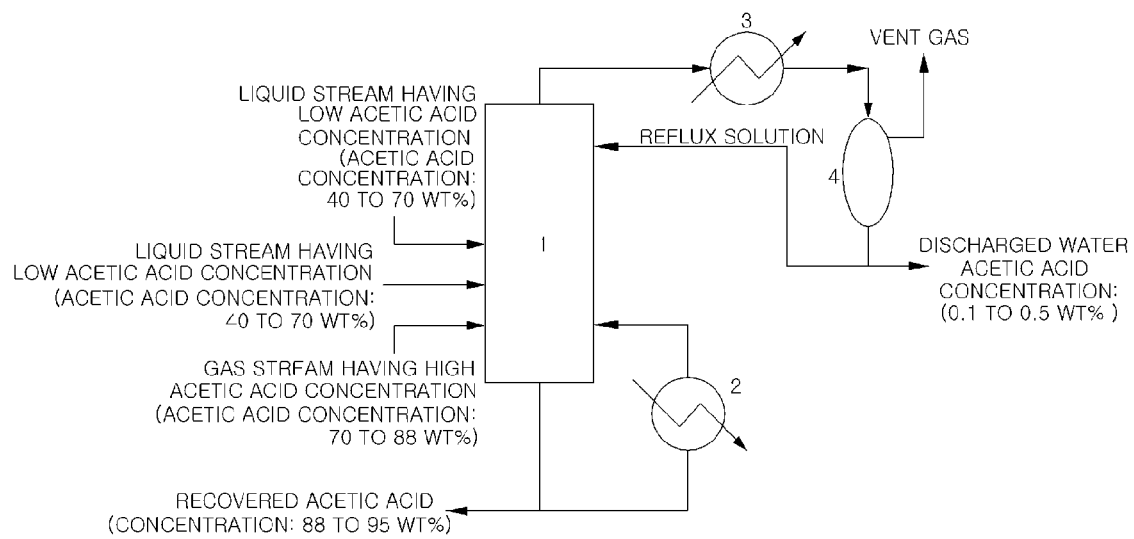
FIG. 1 is a diagram for describing a method of recovering an acetic acid through conventional distillation using one dehydration tower.
Figure 2:
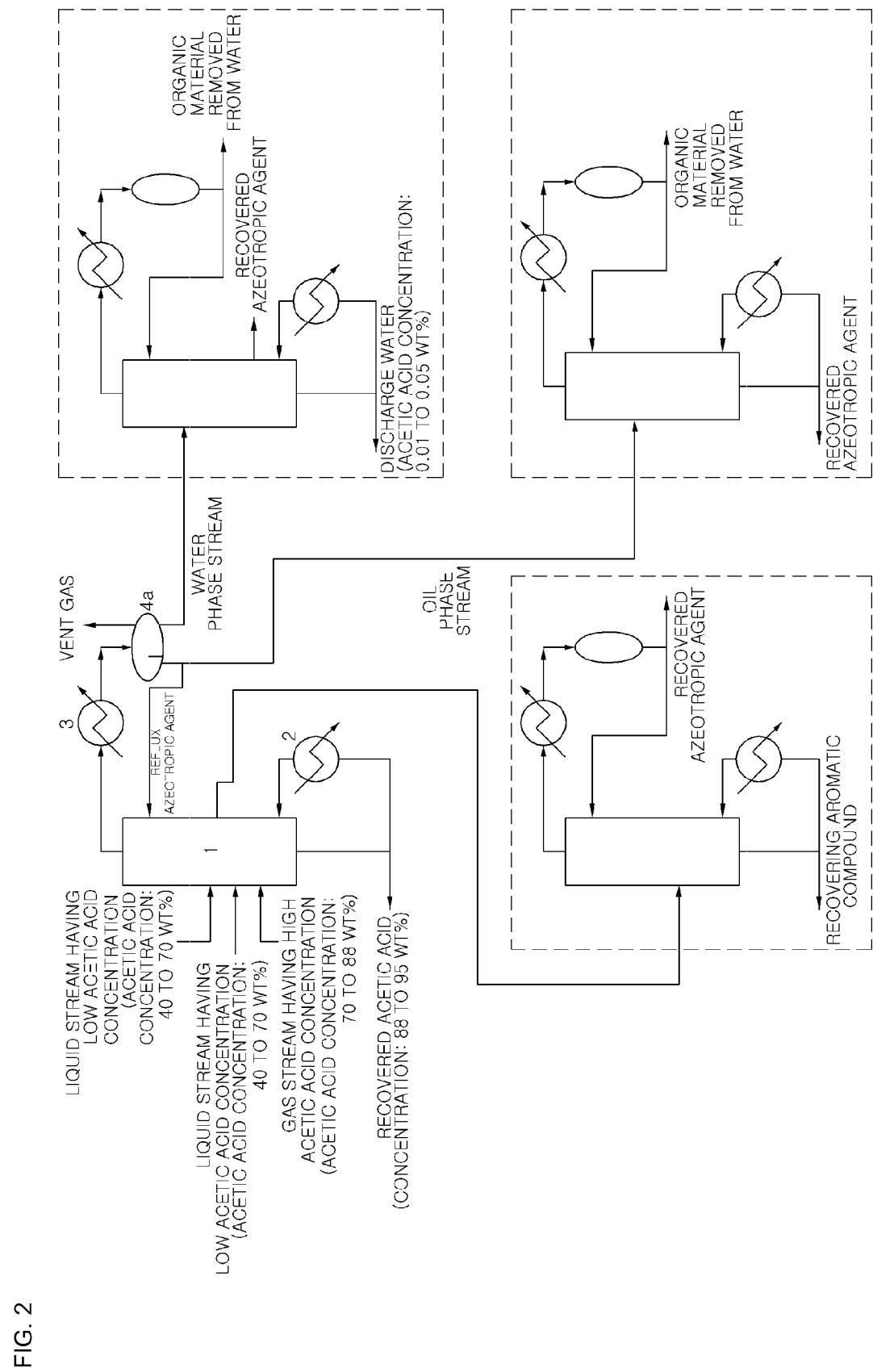
FIG. 2 is a diagram for describing a method of recovering an acetic acid through azeotropic distillation using one dehydration tower.
Figure 3:
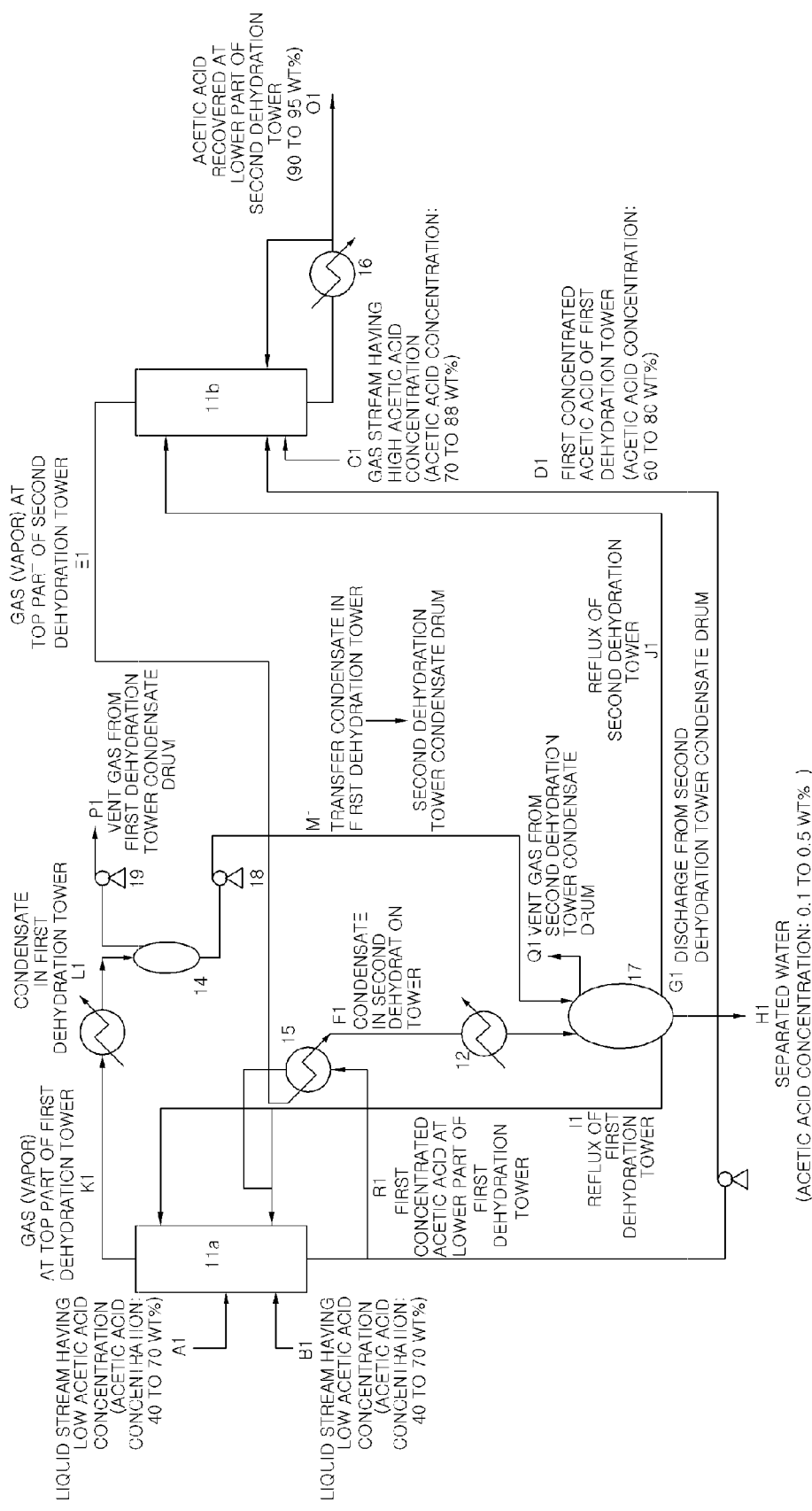
FIG. 3 is a diagram for describing a method of separating off water and recovering a carboxylic acid (acetic acid) from a reactor discharge during oxidation of an aromatic compound by using two dehydration towers sharing energy, according to an embodiment of the present invention.

FIG. 3 is a diagram for describing a method of separating off water and recovering a carboxylic acid (acetic acid) from a reactor discharge during oxidation of an aromatic compound by using two dehydration towers sharing energy, according to an embodiment of the present invention.

As shown in FIG. 3, an apparatus for separating off water and recovering an acetic acid from gases and liquids discharged from a reactor while manufacturing a phthalic acid by using two dehydration towers sharing energy includes first and second dehydration towers 11a and 11b sharing energy, a first dehydration tower condenser 13 provided at a downstream of a top part of the first dehydration tower 11a, a first dehydration tower condensate drum 14 selectively provided at a downstream of the first dehydration tower condenser 13, a first dehydration tower condensate transfer pump 18 and a first dehydration tower condensate vacuum pump 19, a first dehydration tower reboiler-second dehydration tower condenser (energy sharing heat exchanger) 15 that re-boils and condenses discharges by being commonly connected to a downstream of a lower part of the first dehydration tower 11a and a downstream of a top part of the second dehydration tower 11b, a second dehydration tower cooler 12 and a selectively provided second dehydration tower condensate drum 17 that are sequentially provided at a downstream of the energy sharing heat exchanger 15, and a second dehydration tower reboiler 16 provided at a downstream of a lower part of the second dehydration tower 11b.

By using the apparatus, water may be separated off and a carboxylic acid may be recovered from a discharge discharged from a reactor during oxidation of an aromatic compound.

In other words, the method includes: flowing a discharge into a first dehydration tower that is in a decompressed or atmospheric state after the discharge passes through each device for processes so as to discharge water to a top part of the first dehydration tower and recover a first concentrated carboxylic acid to a lower part of the first dehydration tower (a first operation); and flowing the first concentrated carboxylic acid discharged from the lower part of the first dehydration tower into a center of a second dehydration tower that is in an atmospheric or pressurized state so as to recover a final concentrated carboxylic acid to a lower part of the second dehydration tower (a second operation), wherein a condenser of the second dehydration tower operates as a reboiler of the first dehydration tower such that energy supplied to a reboiler of the second dehydration tower is used as distillation energy of the first dehydration tower.

According to circumstances, a concentrated carboxylic acid may be recovered at a lower part of a first dehydration tower, water containing a carboxylic acid may be discharged to a top part of the first dehydration tower and led into a second dehydration tower to recover a concentrated carboxylic acid at a lower part of the second dehydration tower, and final refined water may be discharged to a top part of the second dehydration tower. In other words, the first and second operations may be switched such that the discharge is first led into the first dehydration tower that is in a decompressed or atmospheric state after passing through each device for processes so as to recover a concentrated carboxylic acid at the lower part of the first dehydration tower and discharge water containing a carboxylic acid to the top part of the first dehydration tower, and that the water containing the carboxylic acid discharged from the top part of the first dehydration tower is then led into the second dehydration tower in an atmospheric or pressurized state so as to recover a concentrated carboxylic acid at the lower part of the second dehydration tower.

A method of separating off water and recovering a carboxylic acid from a reactor discharge during oxidation of an aromatic compound using energy donating coupled distribution, which is performed by the apparatus according to the current embodiment, will now be described in detail. Any stream containing an acetic acid or liquid streams A1 and B1 having low acetic acid concentration from about 40 to about 70 wt % from among reactor discharges that passed through each process are led into the first dehydration tower 11a to separate off water to the top part of the first dehydration tower 11a (M1) and discharge a first concentrated acetic acid to the lower part of the first dehydration tower 11a (R1). Concentration of the first concentrated acetic acid discharged to the lower part of the first dehydration tower 11a is from about 60 to about 80 wt %. A gas stream C1 having high acetic acid concentration from about 70 to about 88 wt % from among the reactor discharges that passed through each process is selectively led into the second dehydration tower 11b, and the first concentrated acetic acid discharged to the lower part of the first dehydration tower 11a is led into the second dehydration tower 11b (D1). Here, steam is used in the second dehydration tower reboiler 16, and the energy sharing heat exchanger 15 operates as a reboiler of the first dehydration tower 11a. Concentration of an acetic acid recovered at the lower part of the second dehydration tower 11b is from 90 to 95 wt %, and concentration of an acetic acid in water separated off at the top parts of the first and second dehydration towers 11a and 11b is 0.1 to 0.5 wt %. Water separated off to the top part of the first dehydration tower 11a and water separated off to the top part of the second dehydration tower 11b may be separately managed by using a corresponding condensate drum, or may be collected at the second dehydration tower condensate drum 17.

A pressure of the first dehydration tower 11a may be from −0.8 to 0.8 kg/cm$^2$G, in detail, from −0.8 to −0.5 kg/cm$^2$G. A pressure that maintains a temperature for the energy sharing heat exchanger 15 to operate as a reboiler of the first dehydration tower 11a is 0.1 to 1.7 kg/cm$^2$G, in detail, from 0.1 to 0.4 kg/cm$^2$G.

When the pressure of the first dehydration tower 11a is too low, it is difficult to operate the first dehydration tower 11a due to limitations to condensate water used at the top part, and when the pressure of the first dehydration tower 11a is too high, the pressure of the second dehydration tower 11b needs to be maintained further higher, thereby increasing a temperature of the lower part of the second dehydration tower 11b, and thus high pressure steam that is expensive needs to be used.

Meanwhile, since the temperature of the first dehydration tower 11a is low, when a separate reboiler is additionally disposed around the first dehydration tower 11a and low pressure steam or vacuum steam that is not used during processes is supplied, consumption of medium pressure steam supplied to the second dehydration tower 11b may be further reduced.

A sufficient operating pressure of the second dehydration tower 11b for transferring energy to the lower part of the first dehydration tower 11a may be maintained.

When the number of dehydration towers is three or more, energy consumption may be further reduced but investment costs are increased whereas an energy reduction effect according to the increased number is reduced, and thus the number of dehydration towers may be two or three.

When 500,000 tons of phthalic acid is generated per year, medium pressure steam used by a dehydration tower having 90 stages of trays used in conventional distillation is 90 to 100 tons per hour, whereas consumption of medium pressure steam is 55 to 65 tons per hour when a conventional dehydration tower is used as a second dehydration tower and a first dehydration tower has 60 stages of trays, by using the method of the current embodiment, i.e., a separating and recovering method including: flowing any stream containing an acetic acid or liquid stream having low acetic acid concentration, which passed through each process, into a first dehydration tower in an atmospheric or decompressed state so as to discharge water to a top part and discharge a first concentrated acetic acid to a lower part; and flowing the first concentrated acetic acid discharged to the lower part of the first dehydration tower into a center of a second dehydration tower to separate off water at a top part and recover a final concentrated acetic acid to a lower part, wherein a condenser of the second dehydration tower operates as a reboiler of the first dehydration tower, while separating off water generated via oxidation and recovering an acetic acid that is a type of a carboxylic acid used as a solvent during a process of manufacturing a phthalic acid that is a type of an aromatic carboxylic acid by oxidizing xylene that is a type of an aromatic compound by air in a reactor. The consumption of medium pressure steam according to the method of the current embodiment is very small even compared to consumption of medium pressure steam when stages of two dehydration towers are added such that one dehydration tower has 150 (90+60) stages, i.e., 80 to 90 tons per hour, and is small compared to consumption of medium pressure steam used in a dehydration tower and an azeotropic agent recovering process during azeotropic distillation, i.e., 65 to 75 tons per hour. Since energy required to decompress a first dehydration tower or to transfer a liquid (water) from the first dehydration tower to a second dehydration tower corresponds to less than 1 ton of medium pressure steam per hour, the consumption of medium pressure steam according to the method of the current embodiment is very small compared to reduced consumption of dehydration tower energy.

Accordingly, when one azeotropic distillation tower is operated, about 70 to 75% of energy used during conventional distillation where one dehydration tower is operated is consumed, and when two dehydration towers sharing energy is operated, about 60 to 65% of energy used during the conventional distillation is consumed.

Stream containing an acetic acid, which is led into first and second dehydration towers, may be selected such that energy supplied to the second dehydration tower and energy required by the first dehydration tower are reduced and balanced while considering acetic acid concentration and temperature of the steam.

Figure 4:
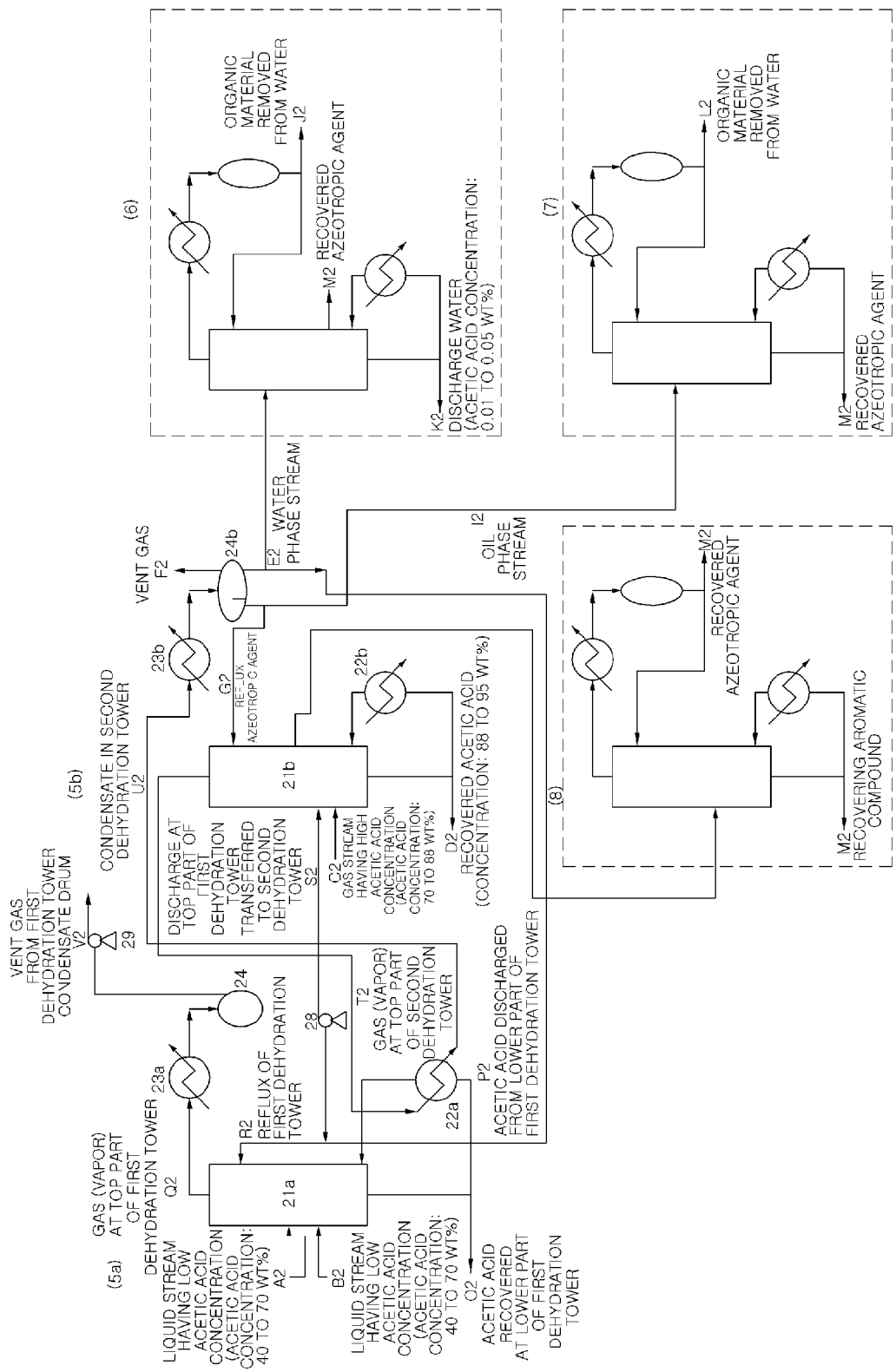
FIG. 4 is a diagram for describing a method of separating off water and recovering a carboxylic acid (acetic acid) from a reactor discharge during oxidation of an aromatic compound by using two dehydration towers sharing energy, according to another embodiment of the present invention, wherein the method includes azeotropic distillation.

FIG. 4 is a diagram for describing a method of separating off water and recovering a carboxylic acid from a reactor discharge during oxidation of an aromatic compound by using two dehydration towers sharing energy, according to another embodiment of the present invention, wherein the method includes azeotropic distillation.

As shown in FIG. 4, an apparatus for separating off water and recovering an acetic acid from a gas and a liquid discharged from a reactor while manufacturing a phthalic acid by using two dehydration towers sharing energy when azeotropic distillation is included, the apparatus includes: a first acetic acid recovering device 5a including a first dehydration tower 21a for separating any stream containing an acetic acid or a liquid stream having low acetic acid concentration into an acetic acid and water via conventional distillation, a first condenser 23a for condensing a gas discharged to a top part of the first dehydration tower 21a, a first condensate drum selectively provided to store a condensate that passed through the first condenser 23a, and a first reboiler 22a for supplying energy to the first dehydration tower 21a, wherein the first reboiler 22a shares energy with a second condenser 23b at a top part of a second dehydration tower 21b that is an azeotropic distillation tower; and a second acetic acid recovering device 5b provided at the rear of the first acetic acid recovering device 5a and including the second dehydration tower 21b for azeotropic distillation into which a gas stream having high acetic acid concentration is selectively led and into which a discharge from the first dehydration tower 21a is led, the second condenser 23b for condensing a gas discharged to a top part of the second dehydration tower 21b through the first reboiler 22a, an oil separator 24a provided at a rear of the second condenser 23b, and a second reboiler 22b for supplying energy to the second dehydration tower 21b, wherein the apparatus selectively includes the organic material recovering device 6 for recovering an organic material from a water phase stream from the second acetic acid recovering device 5b, the azeotropic agent recovering device 7 for recovering an azeotropic agent from an oil phase stream of the second acetic acid recovering device 5b, and the aromatic compound recovering device 8 for recovering an aromatic compound from the second acetic acid recovering device 5b. According to the current embodiment, in a condensate drum 24 of the first acetic acid recovering device 5a, a vacuum pump 29 is selectively provided at one side of a downstream so that a vent gas is discharged, and a transfer pump 28 is selectively provided at the other side of the downstream so that a discharge condensate is led into the second dehydration tower 21b. According to the current embodiment, the organic material recovering device 6, the azeotropic agent recovering device 7, and the aromatic compound recovering device 8 each include a distillation tower, a reboiler, a condenser, and a condensate drum, which are basic components for recovering an acetic acid through conventional distillation.

By using the apparatus, water may be separated off and a carboxylic acid may be recovered from a discharge discharged from a reactor during oxidation of an aromatic compound using energy donating coupled distillation.

In other words, when a second dehydration tower operated in an atmospheric or pressurized state is configured as an azeotropic distillation tower, the method includes: flowing a discharge into a first dehydration tower that is in a decompressed or atmospheric state after the discharge passes through each device for processes so as to recover concentrated carboxylic acid at a lower part of the first dehydration tower and discharge water from which a carboxylic acid is not fully removed to a top part of the first dehydration tower (a first operation); and flowing the water discharged to the top part of the first dehydration tower into a center of the second dehydration tower in an atmospheric or pressurized state, wherein the second dehydration tower is configured as an azeotropic distillation tower, so as to recover a carboxylic acid at a lower part of the second dehydration tower and discharge finally separated water to a top part of the second dehydration tower (a second operation), wherein a condenser of the second dehydration tower operates as a reboiler of the first dehydration tower such that energy supplied to a reboiler of the second dehydration tower is used as distillation energy of the first dehydration tower.

According to circumstances, refined water may be discharged to the top part of the first dehydration tower, a first concentrated carboxylic acid may be discharged to the lower part of the first dehydration tower and led into the second dehydration tower to recover a final concentrated carboxylic acid at the lower part of the second dehydration tower, and refined water may also be discharged to the top part of the second dehydration tower. In other words, the first and second operations may be switched such that the discharge is led into the first dehydration tower in the decompressed or atmospheric pressure after passing through each device to discharge refined water to the top part of the first dehydration tower and discharge the first concentrated acetic acid to the lower part of the first dehydration tower in the first operation, and that the first concentrated acetic acid discharged to the lower part of the first dehydration tower is led into the center of the second dehydration tower in the atmospheric or pressurized state to recover the final concentrated acetic acid at the lower part of the second dehydration tower and to discharge refined water to the top part of the second dehydration tower in the second operation, wherein the second dehydration tower is configured as an azeotropic distillation tower.

When the second dehydration tower 21b is configured as an azeotropic distillation tower according to the current embodiment, in the method of separating off water and recovering an acetic acid from a gas and a liquid discharged from a reactor while manufacturing a phthalic acid by using two dehydration towers sharing energy as shown in FIG. 4, any stream containing an acetic acid or liquid stream A2 and B2 having low acetic acid concentration from about 40 to about 70 wt % from among reactor discharges that passed through each process are led into the first dehydration tower 21a so as to recover an acetic acid at the lower part of the first dehydration tower (O2) and discharge water from which an acetic acid is firstly removed to the top part of the first dehydration tower (Q2). Concentration of an acetic acid in the water discharged to the top part of the first dehydration tower is from about 20 to about 60 wt %. A gas stream C2 having high acetic acid concentration from about 70 to about 88 wt % from among the reactor discharges that passed through each process is selectively led into the second dehydration tower 21b and the water discharged to the top part of the first dehydration tower 21a is led into the second dehydration tower 21b (S2). Here, steam is used in the second reboiler 22b of the second dehydration tower 21b, and the second condenser 23b of the second dehydration tower 21b operates as a reboiler of the first dehydration tower 21a. Concentration of an acetic acid recovered at the lower part of the second dehydration tower 21b is from 90 to 95 wt %, and concentration of an acetic acid in water separated off at the top part of the second dehydration tower 21b is 0.01 to 0.05 wt %, in detail, 0.005 to 0.03 wt %. An upstream of the first dehydration tower 21a may be used as a reflux of the first dehydration tower 21a and an upstream of the second dehydration tower 21b may be used as a reflux of the second dehydration tower 21b and may also be used as a reflux of the first dehydration tower 21a since acetic acid concentration in water at the top part of the second dehydration tower 21b is low. As described above, an azeotropic agent is refluxed in the second dehydration tower 21b (G2).

A pressure of the first dehydration tower 21a may be from −0.8 to 0.8 kg/cm$^2$G, in detail, from −0.8 to −0.5 kg/cm$^2$G. A pressure that maintains a temperature for the second condenser 23b of the second dehydration tower 21b to operate as a reboiler of the first dehydration tower 21a is 0.1 to 1.7 kg/cm$^2$G, in detail, from 0.1 to 0.4 kg/cm$^2$G.

When the pressure of the first dehydration tower 21a is too low, it is difficult to operate the first dehydration tower 21a due to limitations to condensate water used at the top part, and when the pressure of the first dehydration tower 21a is too high, the pressure of the second dehydration tower 21b needs to be maintained further higher, thereby increasing a temperature of the lower part of the second dehydration tower 21b, and thus high pressure steam that is expensive needs to be used. Since the temperature of the first dehydration tower 21a is low, when a reboiler of the first dehydration tower 21a is additionally disposed and low pressure steam or vacuum steam that is not used during processes is supplied, consumption of medium pressure steam supplied to the second dehydration tower 21b may be further reduced.

A sufficient operating pressure of the second dehydration tower 21b for transferring energy to the lower part of the first dehydration tower 21a may be maintained.

When the number of dehydration towers is three or more, energy consumption may be further reduced but investment costs are increased whereas an energy reduction effect according to the increased number is reduced, and thus the number of dehydration towers may be two or three.

Examples of an azeotropic agent used in a second dehydration tower include acetate-based compounds, such as acetylacetate-based, propylacetate-based, and butylacetate-based compounds, alcohol-based compounds, such as butylalcohol-based compounds, aromatic compounds, such as xylene-based compounds, and mixtures thereof.

Stream containing an acetic acid, which is led into first and second dehydration towers, may be selected such that energy supplied to the second dehydration tower and energy required by the first dehydration tower are reduced and balanced while considering acetic acid concentration and temperature of the steam.

Figure 5:
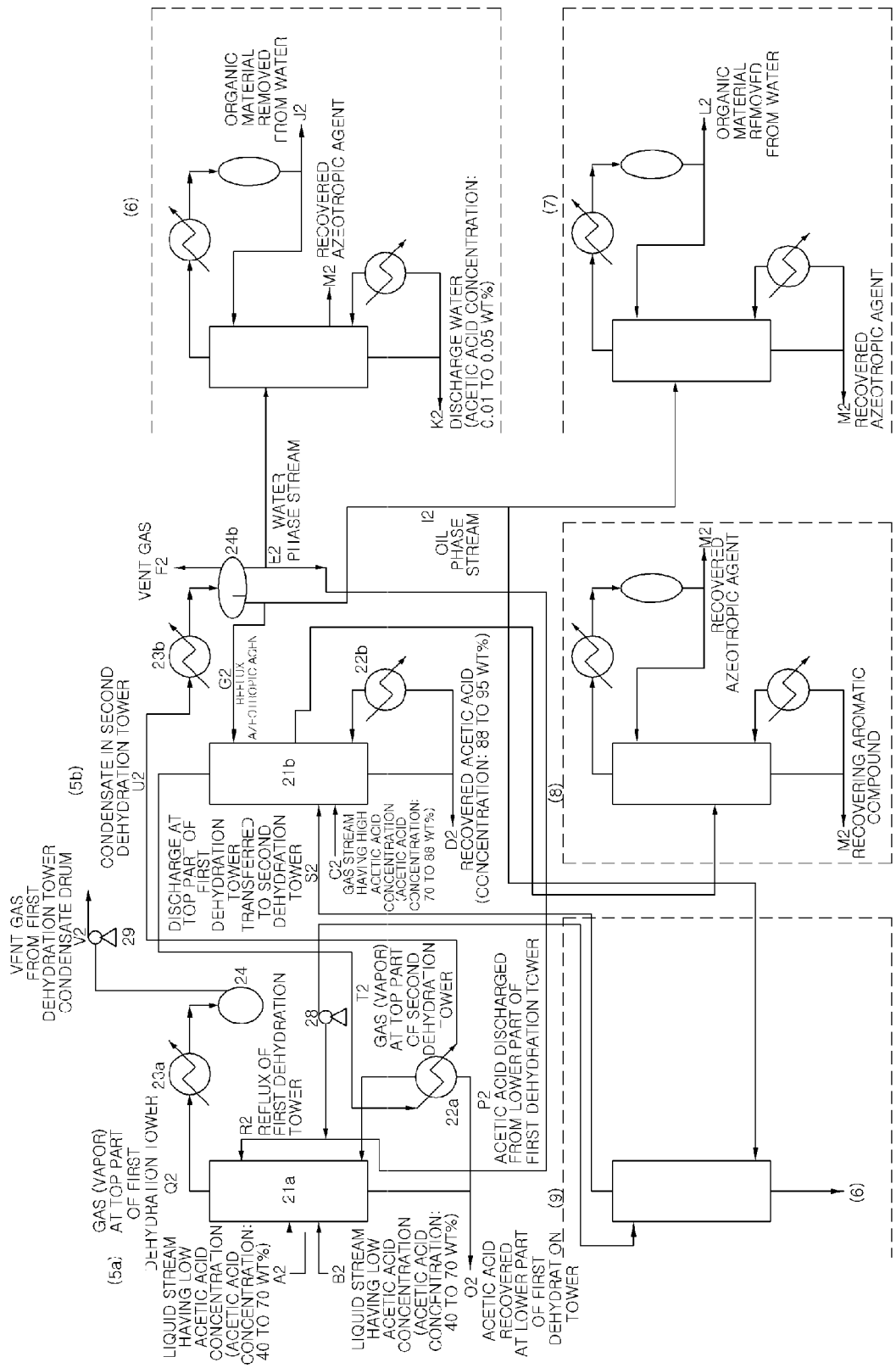
FIG. 5 is a diagram for describing a method of separating off water and recovering a carboxylic acid (acetic acid) from a reactor discharge during oxidation of an aromatic compound by using two dehydration towers sharing energy, according to another embodiment of the present invention, wherein the method includes azeotropic distillation and an extracting device is added to the diagram of FIG. 4.

FIG. 5 is a diagram for describing a method of separating off water and recovering a carboxylic acid (acetic acid) from a reactor discharge during oxidation of an aromatic compound by using two dehydration towers sharing energy, according to another embodiment of the present invention, wherein the method includes extraction and azeotropic distillation.

The method of separating off water and recovering a carboxylic acid (acetic acid) from a reactor discharge during oxidation of an aromatic compound by using two dehydration towers sharing energy according to the current embodiment of FIG. 5 includes extraction and azeotropic distillation, wherein an extracting device 9 is added to the apparatus of FIG. 4. Since conditions and descriptions of the apparatuses and operations of FIGS. 4 and 5 are similar, overlapping descriptions are not repeated and only additional details are described.

As shown in FIG. 5, when azeotropic distillation is included according to the current embodiment, an apparatus for separating off water and recovering an acetic acid from a gas and a liquid discharged from a reactor while manufacturing a phthalic acid by using two dehydration towers sharing energy includes, in addition to components described with reference to FIG. 4, the extracting device 9 in which water containing a low concentration acetic acid discharged from the top part of the first dehydration tower 21a of the first acetic acid recovering device 5a is led into the top part and the azeotropic agent discharged to the top part of the second dehydration tower 21b of the second acetic acid recovering device 5b is led into the lower part as an extracting agent such that the top part transfers a mixture of the extracting agent, the acetic acid, and the water to the second dehydration tower 21b and the lower part selectively transfers the water to the organic material recovering device 6.

In other words, an apparatus for separating off water and recovering a carboxylic acid from a discharge discharged from a reactor during oxidation of an aromatic compound using energy donating coupled distillation includes: the first carboxylic acid recovering device 5a including a first dehydration tower for separating a carboxylic acid and water via conventional distillation, a first condenser for condensing a gas discharged to a top part of the first dehydration tower, a first condensate drum selectively provided to store a condensate that passed through the first condenser, and a first reboiler for supplying energy to the first dehydration tower, wherein the first reboiler shares energy with a second condenser at a top part of a second dehydration tower that is an azeotropic distillation tower; and the second carboxylic acid recovering device 5b provided at the rear of the first carboxylic acid recovering device 5a and including the second dehydration tower for azeotropic distillation into which a stream formed of another carboxylic acid and water is selectively led and into which a discharge from an extraction tower is led, the second condenser for condensing a gas discharged to a top part of the second dehydration tower through the first reboiler, an oil separator provided at a rear of the second condenser, and a second reboiler for supplying energy to the second dehydration tower, wherein the apparatus selectively includes the organic material recovering device 6 for recovering an organic material from a water phase stream from the second carboxylic acid recovering device 5b, the azeotropic agent recovering device 7 for recovering an azeotropic agent from an oil phase stream of the second carboxylic acid recovering device 5b, the aromatic compound recovering device 8 for recovering an aromatic compound from the second carboxylic acid recovering device 5b, and the extracting device 9 in which water containing a low concentration carboxylic acid discharged from a top part of the first dehydration tower of the first carboxylic acid recovering device 5a is led into a top part and an azeotropic agent discharged to a top part of the second dehydration tower of the second carboxylic acid recovering device 5b is led into a lower part as an extracting agent such that the top part transfers a mixture of the extracting agent, the carboxylic acid, and the water to the second dehydration tower and the lower part selectively transfers the water to the organic material recovering device 6.

According to the current embodiment, in the condensate drum 24 of the first acetic acid recovering device 5a, the vacuum pump 29 is selectively provided at one side of a downstream so that a vent gas is discharged, and the transfer pump 28 is selectively provided at the other side of the downstream so that a discharge condensate is led into the second dehydration tower 21b. Also, the organic material recovering device 6, the azeotropic agent recovering device 7, and the aromatic compound recovering device 8 each include a distillation tower, a reboiler, a condenser, and a condensate drum, which are basic components for recovering an acetic acid through conventional distillation, and the extracting device 9 also includes an extraction tower generally using an extracting agent.

By using the apparatus, water may be efficiently separated off and a carboxylic acid may be recovered from a discharge discharged from a reactor during oxidation of an aromatic compound using energy donating coupled distillation.

In other words, when a second dehydration tower operated in an atmospheric or pressurized state is configured as an azeotropic distillation tower, a method of separating off water and recovering a carboxylic acid from a discharge discharged from a reactor during oxidation of an aromatic compound using energy donating coupled distillation includes: flowing the discharge into a first dehydration tower that is in a decompressed or atmospheric state after the discharge passes through each device for processes so as to recover a concentrated carboxylic acid at a lower part of the first dehydration tower and discharge water from which a carboxylic acid is not fully removed to a top part of the first dehydration tower (a first operation); flowing water containing a carboxylic acid discharged to the top part of the first dehydration tower into a top part of an extraction tower and flowing an azeotropic agent discharged from an oil separator provided at a downstream of a top part of a second dehydration tower into a lower part of the extraction tower as an extracting agent so as to discharge water from which a carboxylic acid is removed to the lower part of the extraction tower and extract a mixture of the extracting agent, the carboxylic acid, and the water to the top part of the extraction tower (a second operation); and flowing the mixture discharged to the top part of the extraction tower into a center of the second dehydration tower in an atmospheric or pressurized state, wherein the second dehydration tower is configured as an azeotropic distillation tower, so as to recover a carboxylic acid at a lower part of the second dehydration tower and discharge finally separated water to a top part of the second dehydration tower by using an azeotropic agent (a third operation), wherein a condenser of the second dehydration tower operates as a reboiler of the first dehydration tower such that energy supplied to a reboiler of the second dehydration tower is used as distillation energy of the first dehydration tower.

According to the method of the current embodiment, by further performing the extracting process as well as processes according to the previous embodiment, the condenser of the second dehydration tower operates as the reboiler of the first dehydration tower, such that energy supplied to the reboiler of the second dehydration tower may also be used as distillation energy of the first dehydration tower.

The extracting process will now be described in detail. First, an acetic acid from which water is removed (acetic acid concentration: 90 to 95%) is recovered at the lower part of the first dehydration tower 21a, water having acetic acid concentration of 15 to 50% is discharged to the top part (here, if the acetic acid concentration is too low, the first dehydration tower 21a may not be operated by only using energy supplied from the second dehydration tower 21b, and thus energy may need to be additionally supplied, and if the acetic acid concentration is too high, it may be difficult for the extraction tower to select an extracting agent), water discharged to the top part of the first dehydration tower is led into the top part of the extraction tower, water from which an acetic acid is removed is selectively discharged to the lower part of the extraction tower by using the azeotropic agent discharged to the top part of the second dehydration tower as an extracting agent, and the extracting agent containing an acetic acid and some water is discharged from the top part of the extraction tower to the second dehydration tower 21 (the azeotropic agent used in the second dehydration tower may be used as the extracting agent of the extraction tower, but a separate extracting agent may be used according to characteristics of factories).

As such, a mixture of an extracting agent, an acetic acid, and water, which is discharged to a top part of an extraction tower is transferred to a second dehydration tower such that an acetic acid is recovered (90 to 95%) at a lower part of the second dehydration tower, a mixture of water and an azeotropic agent is discharged to a top part of the second dehydration tower as a gas to be transferred a second condenser through a first condenser (energy heat exchanger) of the second dehydration tower, and since water discharged to a lower part of the extraction tower has acetic acid concentration from about 100 to about 500 wt.ppm and extracting agent concentration from 0.1 to 5 wt %, the water is transferred for a distillation process for recovering an organic material from a water phase stream to recover an organic material and discharge waste water.

Process conditions of the current embodiment according to FIG. 5 are the same as those of the previous embodiment according to FIG. 4.

In summary, according to the method of separating off water and recovering a carboxylic acid from a discharge discharged from a reactor during oxidation of an aromatic compound using energy donating coupled distillation, at least two dehydration towers having different operating pressures may be used such that a condenser of one dehydration tower operates as a reboiler of the other dehydration tower, at least two dehydration towers may be configured as a distillation tower for conventional distillation, at least one of the at least two dehydration towers may be configured as an azeotropic distillation tower, or vacuum steam or low pressure steam may be used as a heat source supplied to a reboiler of at least one of the at least two dehydration towers.

While the present invention has been particularly shown and described with reference to exemplary embodiments thereof, it will be understood by those of ordinary skill in the art that various changes in form and details may be made therein without departing from the spirit and scope of the present invention as defined by the following claims.

| <Explanation of Reference Numerals> | |
|---|---|
| 1, 11, 21: Dehydration Tower (Distillation Tower) | 2, 15, 16, 22: Reboiler |
| 3, 13, 23: Condenser | 4, 14, 17, 24: Condensate Drum |
| 4a, 24b: Oil Separator | 5: Carboxylic Acid (Acetic Acid) Recovering Device |
| 6: Organic Material Recovering Device | 7: Azeotropic agent Recovering Device |
| 8: Aromatic Compound Recovering Device | 9: Extracting Device |
| 18, 28: Transfer Pump | 19, 29: Vacuum Pump |

The invention claimed is:

1. A method of separating off water and recovering acetic acid from a discharge discharged from a reactor during oxidation of a phthalic acid compound, the method comprising:
    flowing the discharge into a first dehydration tower that is in a decompressed or atmospheric state after the discharge passes through each device for processes so as to discharge water to a top part of the first dehydration tower, and recovering a first concentrated acetic acid from a lower part of the first dehydration tower; and
    flowing the first concentrated acetic acid discharged from the lower part of the first dehydration tower into a center of a second dehydration tower that is in an atmospheric or pressurized state so as to recover a final concentrated acetic acid from a lower part of the second dehydration tower,
    wherein working pressures of the first dehydration tower and the second dehydration tower are respectively from −0.8 to −0.5 kg/cm$^2$G and from 0.1 to 1.7 kg/cm$^2$G, and a condenser of the second dehydration tower operates as a reboiler of the first dehydration tower using the different pressure between the first dehydration tower and the second dehydration tower.

2. A method of separating off water and recovering acetic acid from a discharge discharged from a reactor during oxidation of a phthalic acid compound, the method comprising:
    flowing the discharge into a first dehydration tower that is in a decompressed or atmospheric state after the discharge passes through each device so as to recover a concentrated acetic acid at a lower part of the first dehydration tower, and discharge water from which acetic acid is not fully removed to a top part of the first dehydration tower; and
    flowing the water discharged to the top part of the first dehydration tower into a center of a second dehydration tower in an atmospheric or pressurized state, wherein the second dehydration tower is organized as an azeotropic distillation tower, so as to recover a acetic acid at a lower part of the second dehydration tower and discharge finally separated water to a top part of the second dehydration tower by using an azeotropic agent,
wherein working pressures of the first dehydration tower and the second dehydration tower are respectively from −0.8 to −0.5 kg/cm²G and from 0.1 to 1.7 kg/cm²G, and a condenser of the second dehydration tower operates as a reboiler of the first dehydration tower using the different pressure between the first dehydration tower and the second dehydration tower.

3. A method of separating off water and recovering acetic acid from a discharge discharged from a reactor during oxidation of a phthalic acid compound, the method comprising:
flowing the discharge into a first dehydration tower that is in a decompressed or atmospheric state after the discharge passes through each device for processes so as to recover a concentrated acetic acid at a lower part of the first dehydration tower and discharge water from which a acetic acid is not fully removed to a top part of the first dehydration tower;
flowing water containing a acetic acid discharged to the top part of the first dehydration tower into a top part of an extraction tower and flowing an azeotropic agent discharged from an oil separator provided at a downstream of a top part of a second dehydration tower into a lower part of the extraction tower as an extracting agent so as to discharge water from which a acetic acid is removed to the lower part of the extraction tower and extract a mixture of the extracting agent, the acetic acid, and the water to the top part of the extraction tower; and
flowing the mixture discharged to the top part of the extraction tower into a center of the second dehydration tower in an atmospheric or pressurized state, wherein the second dehydration tower is organized as an azeotropic distillation tower, so as to recover acetic acid at a lower part of the second dehydration tower and discharge finally separated water to a top part of the second dehydration tower by using an azeotropic agent, and the mixture comprises the extracting agent, the acetic acid and the water,
wherein working pressures of the first dehydration tower and the second dehydration tower are respectively from −0.8 to −0.5 kg/cm²G and from 0.1 to 1.7 kg/cm²G, and a condenser of the second dehydration tower operates as a reboiler of the first dehydration tower using the different pressure between the first dehydration tower and the second dehydration tower.

* * * * *